United States Patent [19]

Watanabe

[11] Patent Number: 5,792,655
[45] Date of Patent: Aug. 11, 1998

[54] METHOD FOR CULTURING T LINEAGE PRECURSOR CELLS UNDER CONDITIONS OF HIGH OXYGEN CONCENTRATION

[75] Inventor: Yoshihiro Watanabe, Yokohama, Japan

[73] Assignee: Japan Tobacco, Inc., Tokyo, Japan

[21] Appl. No.: 526,084

[22] Filed: Sep. 11, 1995

Related U.S. Application Data

[63] Continuation of Ser. No. 983,514, filed as PCT/JP92/00829 Jul. 1, 1992, Pat. No. 5,476,780.

[30] Foreign Application Priority Data

Jul. 4, 1991 [JP] Japan ................... 3-258283

[51] Int. Cl.$^6$ .................. C12N 5/00; C12N 5/06; C12N 5/08
[52] U.S. Cl. .................. 435/325; 435/326; 435/366; 435/372.7; 435/372.3; 435/384
[58] Field of Search .................. 435/325, 326, 435/366, 372.2, 372.3, 384

[56] References Cited

U.S. PATENT DOCUMENTS

| | | | |
|---|---|---|---|
| 4,284,724 | 8/1981 | Fukuda | 435/255 |
| 4,448,879 | 5/1984 | Fabricius | 435/240.2 |
| 4,649,114 | 3/1987 | Miltenburger | 435/240 |
| 4,720,462 | 1/1988 | Rosenson | 435/285 |
| 5,147,784 | 9/1992 | Peault | 435/240.2 |

FOREIGN PATENT DOCUMENTS

| | | |
|---|---|---|
| 0092566 | 5/1986 | Japan . |
| A61-166393 | 7/1986 | Japan . |
| A2-131572 | 5/1990 | Japan . |
| 3108479 | 5/1991 | Japan . |
| 8706610 | 11/1987 | WIPO . |

OTHER PUBLICATIONS

PCT/US89/02233, filed May 22, 1989 (equiv. to WO 89/11530) "Growth of Animal Cells at High Oxygen Concentration".
Muench et al., Cytokine, vol. 4, No. 6, pp. 488–494 Nov. 1992.
Effect of Deoxyguanosine on Lymphopoiesis . . . , Eur. J. Immunol., 1982, 12:583–587.
"Requirement of Dendritic Cells and B Cells . . . ", Osam Mazda, Rockefeller U. Press, vol. 173, Mar. 1991, pp. 539–547.
"Autoimmune Diseases" The Failure of Self Tolerance, Sinha et al., Science, vol. 248, Jun. 1990.
"Autoimmunity to Collagen II and Myelin Basic Protein . . . ", Klareskog et al., Immunol. Rev. 1990, No. 118.
"Autoimmunity, Microbial Immunity and the Immunological Homunculus", Cohen et al., Immun. Today, vol. 12, #4, 1991.
"T–cell Recognition of an Immuno–dominant Myelin . . . ", Ota et al., Nature, vol. 346, Jul. 12, 1990.
"Recovery from Autoimmunity of Mrl/lpr Mice . . . " Gutierrez–Ramos et al., Nature, vol. 346, Jul. 19, 1990.
Galili et al. "Human Prothymocytes", J. Exp. Med. vol. 152, pp. 796–807, 1980.
Green et al. Production and Characterization of Human T–Cell Hybrid . . . , Clinical Research, vol. 29, #2, 368A, 1981.
Ceredig et al., "Mouse Fetal Thymus Lobes Cultured . . . ", J. Immun., vol. 142, #10, 1989, pp. 3353–3360.
Cattermale, J. et al., "Isolation of Murine Fetal Thymus . . . " J. Immunol., vol. 142, #11, 1989, pp. 3746–3753.
Aparicio, P. et al., "Isolation and Characterization . . . " J. Exp. Med., vol. 170, pp. 1009–1014 , 1989.
Leclercq, G., et al., "Preferential Proliferation of T Cell . . . " vol. 145, #12, pp. 3992–3997, 1990.
Kingston et al., Nature, vol. 317, pp. 811–813, 1985.
Oller et al., J. of Cell Science, vol. 94, pp. 43–49 (1989).
Smith et al., British Journal of Haematology, vol. 63, pp. 29–34 (1986).
Palsson et al., Bio/Technology, vol. 11, pp. 368–372 (Mar. 1993).
Kuby 1994 Immunology, Second Edition. W.H. Freeman Company, New York pp. 273–294, Jan. 1, 1994.

Primary Examiner—Marian C. Knode
Assistant Examiner—Mary K. Zeman
Attorney, Agent, or Firm—Birch, Stewart, Kolasch & Birch, LLP

[57] ABSTRACT

The present invention provides culture methods of T lineage precursor cells comprising a step of culturing the T lineage precursor cells under a condition that a dissolved oxygen concentration in the nutrient medium is higher than a dissolved oxygen concentration in the nutrient medium when the medium is in contact with normal atmospheric air. According to the methods of the present invention, by using a submerged (suspension) culture which is a general method for culturing cells or tissues, the derivation of matured T cell(s) differentiated from T precursor cells in terms of their phenotypes of differentiation antigens and of their functions is realized to be accomplished.

9 Claims, 12 Drawing Sheets

1

METHOD FOR CULTURING T LINEAGE PRECURSOR CELLS UNDER CONDITIONS OF HIGH OXYGEN CONCENTRATION

This application is a continuation divisional of application Ser. No. 07/983,514, filed as PCT/JP92/00829 Jul. 1, 1992, now U.S. Pat. No. 5,476,780, the entire contents of which are hereby incorporated by reference.

[TECHNICAL FIELD]

The present invention relates to a method for culturing T lineage precursor cells, which enables derivation and generation of matured T cells differentiated from the T lineage precursor cells. The invention further relates to: T cells obtained by using this method.

[BACKGROUND ART]

The earliest of T cells exist mainly in bone marrow or fetal liver, as a form of lymphoid stem cells differentiated from hematopoietic stem cells having an ability to differentiate into multilineage cells. These earliest stem cells emigrate to thymus and mature into T cells through a series of differentiation stages. The differentiation and maturation of the T precursor cells are greatly under the influence of thymic stromal cells. After T precursor cells enter into the thymic cortex, the T precursor cells differentiate and mature into T cells through rapid cell division and proliferation under the control of adhesion with stromal cells comprising mainly thymic epithelial cells which participate in differentiation and maturation of the T precursor cells, adhesion with myeloid cells such as macrophages, and humoral factors produced therefrom. After undergoing several differentiation stages thymocytes flow out to the bloodstream from the cortico-medullary junction of thymus, and emigrate to peripheral lymphoid organs. The emigrated thymocytes, i.e., T cells, further differentiate and mature therein.

To study the detailed process of differentiation and maturation of the T precursor cells, a culture system capable of achieving in-vitro proliferation, differentiation, and maturation of T cells is required.

On the other hand, it is considered that abnormality of differentiation or of functions of T cells due to immunization with infectious bacteria and/or an foreign antigen is one great cause of allergic diseases or various autoimmune diseases. (e.g., Animesh A. et al, Science, vol. 248, 1380–1388, 1990; Irun R. Cohen et al, *Immunology Today*, vol. 12, No. 4, 105–110, 1991; and Lars Klareskog et al, *Immunological Reviews*, vol. 118, 285–310, 1990).

At present, as therapeutic drugs for such diseases, non-specific anti-inflammatory agents and immunosuppressants of T cell functions are used as suppressors. However, essential cure of the diseases has not been achieved due to their non-specificity.

To overcome these problems, extensive studies on vaccine therapy and serum vaccine therapy have been made, comprising respectively (1) specifying an antigen which causes disease and applying the antigen, and (2) specifying said antigen and applying suppressive factors specific for the diseases which are represented by antibodies against the antigen. A cell vaccine therapy using T cells whose antigen specificities has been proved is considered to be an effective therapeutic method for diseases which is assumed to be caused by abnormal differentiation and functional abnormality of T cells (e.g., Jose C. Gutierrez-Ramos et al, Nature, vol. 346, 271–274, 1990 and Kohei Ota et al, Nature, vol. 346, 183–187, 1990). However, methods capable of deriving T cells having appropriate antigen specificity in vitro are limited to a particular method.

In fact, although a submerged (suspension) culture in which cells or tissues are submerged or suspended in a nutrient medium is well known as a method generally used for culture of cells or tissues, it is impossible to differentiate and mature T precursor cells into T cells in accordance with such a conventional method.

At present, as the sole culture method capable of achieving differentiation and maturation of the T precursor cells, only a so-called "afloat culture" is known, in which a fetal thymus is cultured on an interface between the gas phase and the nutrient medium under atmospheric air whose carbon dioxide concentration is controlled to 5% (e.g., Jenkinsen E. J. et al, *Eur. J. Immunology*, vol. 12, 583, 1982 and Osamu Mazda et al, *J. Exp. Med.*, vol. 173, 539–547, 1991). However, this method requires special tools or apparatuses, and differentiation of cells on the liquid surface side is insufficient. In addition to these drawbacks, this method is not suitable for the culture of the T precursor cells accompanying mass proliferation of cells. Therefore, it is difficult to perform a large scale culture.

Strong demand has, therefore, arisen for developing a culture method capable of realizing and achieving derivation of matured T cells differentiated from T precursor cells in terms of their phenotypes of differentiation antigens and of their functions, by using the submerged (suspension) culture as a general method of culturing cells or tissues.

Japanese Unexamined PCT Application No. 3-504329 discloses a method for proliferating a human B blastic cell line by raising the dissolved oxygen concentration in the culture medium by steadily supplying a desired amount of oxygen into the medium placed in a sealed vessel, through a silicon pipe connected to a gas bomb sealed with a gas mixture containing a desired amount of oxygen. In said culture according to the method, the proliferation of the human B blastic cell line is found but differentiation and maturation of the cells is not achieved. The present invention is capable of achieving proliferation of T precursor cells, and of differentiation and maturation of them in terms of their phenotypes of differentiation antigens and of their functions, by using a simpler culture method than that disclosed in above application under a higher concentration of dissolved oxygen in the medium.

[DISCLOSURE OF INVENTION]

It is an object of the present invention to provide a culture method capable of realizing and achieving derivation of matured T cells, differentiated from T precursor cells in terms of their phenotypes of differentiation antigens and of their functions, by using the submerged (suspension) culture as a general method of culturing cells or tissues.

In order to achieve the object, the present inventors made extensive studies on a method of in-vitro culture of T lineage precursor cells and found that matured T cells, differentiated from T lineage precursor cells in terms of their phenotypes of differentiation antigens or their functions, could very be efficiently and easily derived and generated by culturing T lineage precursor cells under a condition wherein the dissolved oxygen concentration in a nutrient medium was higher than that in the normal atmospheric air, i.e., under a condition of high oxygen concentration, thereby achieving the present invention.

That is, a method of culturing T lineage precursor cells according to the present invention comprises a step of culturing the T lineage precursor cells in a nutrient medium under condition such that the dissolved oxygen concentration in the nutrient medium is higher than that present in the normal atmospheric air.

According to the present invention, by using a submerged (suspension) culture well known as a general method of culturing cells or tissues, matured T cells, normally differentiated from T precursor cells in terms of their phenotypes of differentiation antigens or their functions, can be derived and the T precursor cells can be proliferated. In addition, according to the present invention, the culture can be very easily performed without using special tools or apparatuses, and a large scale culture can be performed.

The present invention is described in detail below.

The terms "T lineage precursor cells", "T precursor cells", "tissue(s) containing T precursor cells", "interstitial cells of lymphoid tissues", "nutrient medium", "dissolved oxygen concentration in nutrient medium", and "matured T cells differentiated in terms of their phenotypes of differentiation antigens or their functions" are defined as follows.

a) "T lineage Precursor cells"

The "T lineage precursor cells" used in the present invention mean "T precursor cells", "tissue(s) containing T precursor cells", or a "combination of the T precursor cells and the interstitial cells of lymphoid cells". The term "T lineage precursor cells" can include hematopoietic stem cells.

The "T lineage precursor cells" can be collected from any tissue(s) having T precursor cells regardless of the species, sex, and age of the donor. Preferably, the T lineage precursor cells can be collected from a mammal such as a rat, a mouse, a rabbit, a horse, or a cow. More preferably, T lineage precursor cells are collected from a fetus or neonate of said mammal, and can be collected from a human.

A population of cells participating in the immune response is generically called immunocompetent cells. Among the immunocompetent cells, T- and B-lineage lymphoid cells are related to antigen memory and play principal roles of immune responses. The present invention relates to the T-lineage cells. The origins of the T-lineage cells are lymphoid stem cells differentiated from hematopoietic stem cells existing mainly in bone marrow or fetal liver, and the lymphoid stem cells develop into T lineage stem cells through differentiation. The T lineage stem cells emigrate to the thymus and mature to T cells having an ability of playing a role of cellular immunity through respective stages of differentiation accompanying proliferation.

The term "T precursor cells" used in the present invention means any T lineage cells at any differentiation stage in a series of differentiation and maturation processes from lymphoid stem cells to matured T cells, as described above. For example, the population of "fetal thymocyte(s)" referred to in this specification contains a large number of T lineage stem cells which have emigrated to thymus, and is very useful as a source of "T precursor cells". The phrase "tissue(s) containing T precursor cells" means tissue(s) containing said "T precursor cells". Specifically, the tissue (s) mean tissue(s) or their fragments originated from, e.g., thymus, bone marrow or liver, and more preferably thymus or bone marrow. The "interstitial cells of lymphoid tissues" mean a cell lineage (e.g., thymic epithelial cells, fibroblasts, and intercellular matrix), except for the "T precursor cells", which supports and surrounds the "T precursor cell" in the "tissue(s) containing the T precursor cells". According to the present invention, "T precursor cells" and "interstitial cells of lymphoid tissues" which are respectively obtained from the same or different individuals of the same or different animal species can be combined to practice the present invention. For example, the present invention is practiced by a combination of fetal thymocytes and thymic interstitial cells. More specifically, the present invention is carried out by a combination of human T precursor cells and mouse thymic interstitial cells, a combination of mouse T precursor cells and human thymic interstitial cells, a combination of human T precursor cells and rat thymic interstitial cells, or a combination of rat T precursor cells and human thymic interstitial cells.

b) "Nutrient Medium"

The "nutrient medium" used in the present invention is employed to differentiate, proliferate, mature, maintain, or preserve the T lineage precursor cells defined in a). Any conventional medium for culturing cells can be used. An example of the nutrient medium is an RPMI-1640 medium or an MEM medium. The nutrient medium can contain, as elemental components, sodium, potassium, calcium, magnesium, phosphorus, chlorine, amino acid(s), vitamin (s), hormone(s), antibiotics, serum, or other chemical components depending on application purposes.

The nutrient medium can contain a cytokine such as interleukin-1, interleukin-2, interleukin-3, interleukin-4, interleukin-5, interleukin-6, interleukin-7, interleukin-8, interleukin-9, interleukin-10, interleukin-11, interleukin-12, TNF (Tumour Necrosis Factor), γ-interferon, a granulocyte macrophage colony-stimulating factor (GM-CSF), a granulocyte colony-stimulating factor (G-CSF), or a macrophage colony-stimulating factor (M-CSF), depending on application purposes. By using nutrient medium containing an antigen which induces infectious diseases due to such as a hepatitis virus, an HIV (Human Immunodeficiency Virus) and so on, allergic diseases and autoimmune diseases, T cell vaccines for suppressing and treating the symptoms of infectious diseases, inflammation, allergy, and autoimmune diseases induced by the antigens can be derived and generated.

c) "Dissolved oxygen Concentration in Nutrient Medium"

The term "dissolved oxygen concentration in nutrient medium" used in the present invention means the concentration of oxygen dissolved in a nutrient medium (liquid phase) for culturing the T lineage precursor cells defined in a). The phrase "dissolved oxygen concentration in nutrient medium under normal atmospheric air" indicates the dissolved oxygen concentration in a nutrient medium saturated with natural atmospheric air which is not artificially modified. Therefore, for example, "the dissolved oxygen concentration in a nutrient medium under the condition that the total pressure of the gas phase contacting the nutrient medium is 1 atm, that the oxygen partial pressure of the gas phase is 0.4 atm, and that the temperature is 37° C." indicates that said dissolved oxygen concentration is twice of that of normal atmospheric air, namely, 1 atm atmospheric air, in accordance with Henry's law which says that the solubility of gas at constant temperature is proportional to its partial pressure as far as the pressure is not so high.

As a means for raising the dissolved oxygen concentration in the medium, any means can be used if the means has a capacity for supplying oxygen to raise the amount of oxygen dissolving in the nutrient medium. In particular, it is preferable to substantially raise the dissolved oxygen concentration in the nutrient medium (liquid phase) by raising the oxygen concentration in the gas phase contacting with the nutrient medium (liquid phase) within the range of 40 vol % through 95 vol %, preferably 60 vol % through 95 vol %.

The oxygen concentration is expressed in different units such as %, atm (atmosphere), mmHg, and M (mol) herein.

Any unit of the oxygen concentrations expressed can be converted into any other. The oxygen concentration in the present invention need not be expressed in a specific unit, as a matter of course.

Since the solubility of oxygen is proportional to the partial pressure of oxygen of the gas phase, it is easily understood for the skilled in the art that the dissolved oxygen concentration in the medium can be raised by slightly elevating the pressure of the gas phase even if the oxygen concentration of the gas phase is 60 vol % or less, or 40 vol % or less.

In case of necessity of replacing a part of the medium during the culture, it is preferable to control, in advance, the dissolved oxygen concentration in a medium for replacement to the same dissolved oxygen concentration in the former medium. Alternatively, the dissolved oxygen concentration in the medium for replacement can be controlled by using air flow containing a high amount of oxygen immediately after the replacement.

d) "Matured T cells Differentiated in Terms of their Phenotypes of Differentiation Antigens or their Functions"

T lineage stem cells differentiated and developed from lymphoid stem cells derived from hematopoietic stem cells proliferate and mature through each stage of differentiation and maturation under the control of adhesion with the thymic interstitial cells and of endogenous humoral factors.

Each stage of differentiation and maturation can be distinguished and classified by the phenotypes based on difference of kinds of differentiation antigens expressed on the cell surface, or by biological functions such as abilities of antigen specific proliferation, B cell activation, cytotoxicity and immunosuppression.

By applying the method of the present invention, it is possible to realize and achieve all stages of differentiation and maturation in vitro using the "T lineage precursor cells" defined in a). The term "matured T cells differentiated in terms of their phenotypes of differentiation antigens or their functions" means T lineage cells in said any stage of differentiation and maturation.

[BRIEF DESCRIPTION OF DRAWINGS]

FIG. 2 is a graph showing the cell distribution of mouse matured T cells,

FIG. 3 is a graph showing the cell distribution of mouse fetal thymocytes immediately after these thymocytes are collected, FIG. 4 is a graph showing the cell distribution after mouse fetal thymuses are cultured by an afloat culture at a 20% oxygen concentration, FIG. 5 is a graph showing the cell distribution after mouse fetal thymuses are cultured by a submerged culture at a 5% oxygen concentration, FIG. 6 is a graph showing the cell distribution after mouse fetal thymuses are cultured by a submerged culture at a 20% oxygen concentration, and FIG. 7 is a graph showing the cell distribution after mouse fetal thymuses are cultured by a submerged culture at a 60% oxygen concentration;

FIG. 8 is a graph showing the cell distribution which represents the expression level of CD4 and/or CD8 of mouse matured T cells, FIG. 9 is a graph showing the cell distribution which represents the expression level of CD4 and/or CD8 of mouse fetal thymocytes immediately after these thymocytes are collected, FIG. 10 is a graph showing the cell distribution which represents the expression level of CD4 and/or CD8 after the mouse fetal thymuses are cultured by an afloat culture at a 20% oxygen concentration, FIG. 11 is a graph showing the cell distribution which represents the expression level of CD4 and/or CD8 after the mouse fetal thymuses are cultured by a submerged culture at a 5% oxygen concentration, FIG. 12 is a graph showing the cell distribution which represents the expression level of CD4 and/or CD8 after the mouse fetal thymuses are cultured by a submerged culture at a 20% oxygen concentration, and FIG. 13 is a graph showing the cell distribution which represents the expression level of CD4 and/or CD8 after the mouse fetal thymuses are cultured by a submerged culture at a 40% oxygen concentration.

FIG. 14 is a graph showing the cell distribution which represents the expression level of CD4 and/or CD8 after the mouse fetal thymuses are cultured by a submerged culture at a 60% oxygen concentration.

FIG. 15 is a graph showing the cell distribution which represents the expression level of CD4 and/or CD8 after the mouse fetal thymuses are cultured by a submerged culture at an 80% oxygen concentration.

[BEST MODE OF CARRYING OUT THE INVENTION]

The embodiments of the present invention are described in detail by way of its examples. The present invention is not limited to the following examples, as a matter of course.

EXAMPLE 1

<1-1> Collection of Mouse Thymus

Thymuses were aseptically collected by an ordinary method from 6-week old C57BL/6 mice (B6 young mice) and 15-day fetuses of B6 mice (available from Nippon SLC Corp.) obtained from time-mated C57BL/6 mice (B6 pregnant mice).

<1-2> Collection of Mouse Thymocytes and Counting

The thymuses of the young mice and the mouse fetal thymuses (FT), which were collected in 1-1, were gently minced with stainless steel mesh to afford young mouse thymocytes and mouse fetal thymocytes.

These thymocytes were suspended in an RPMI-1640 complete medium (available from Gibco Corp.), and the numbers of viable cells present in the suspension were counted by a trypan blue dye exclusion test.

<1-3> Culture of T precursor cells at Various Oxygen Concentrations

The fetal thymocytes (7.0×10$^4$ cells/lobe) obtained from the 15-day fetuses of B6 mice were added to an RPMI-1640 complete medium containing sodium pyruvate, sodium hydrogencarbonate, non-essential amino acids (available from Gibco Corp.), 2-mercaptoethanol, penicillin, streptomycin, and 10% fetal calf serum (FCS) in a 24-wells microtiter plate. The plate was sealed in a plastic vessel (Gaspack available from BBL Corp or Tedler bag available from Seikagaku Kogyo Inc.), and air in the vessel was substituted with gas mixtures (available from Iwatani Sangyo Inc.) respectively containing 5% carbon dioxide and 5% oxygen, 5% carbon dioxide and 20% oxygen, 5% carbon dioxide and 30% oxygen, 5% carbon dioxide and 40% oxygen, 5% carbon dioxide and 60% oxygen, and 5% carbon dioxide and 80% oxygen. The cells were cultured by a submerged culture at 37° C. for 5 days.

In order to compare with the prior art, fetal thymocytes (7.0×10$^4$ cells/lobe) obtained from 15-day fetuses of B6 mice were cultured by an afloat culture under the condition of at a carbon dioxide concentration of 5%, an oxygen concentration of 20% and 37° C. for 5 days on a filter (diameter: 13 mm; pore size: 8 μm available from Nucleopore Corp.) floating in an RPMI-1640 complete medium containing sodium pyruvate, sodium hydrogencarbonate, non-essential amino acids (available from Gibco Corp.), 2-mercaptoethanol, penicillin, streptomycin, and a 10% fetal calf serum (FCS) in a 24 well microtiter plate.

After the culture, the numbers of cells were counted by the trypan blue dye exclusion test as in 1-2 above.

Figure 1:
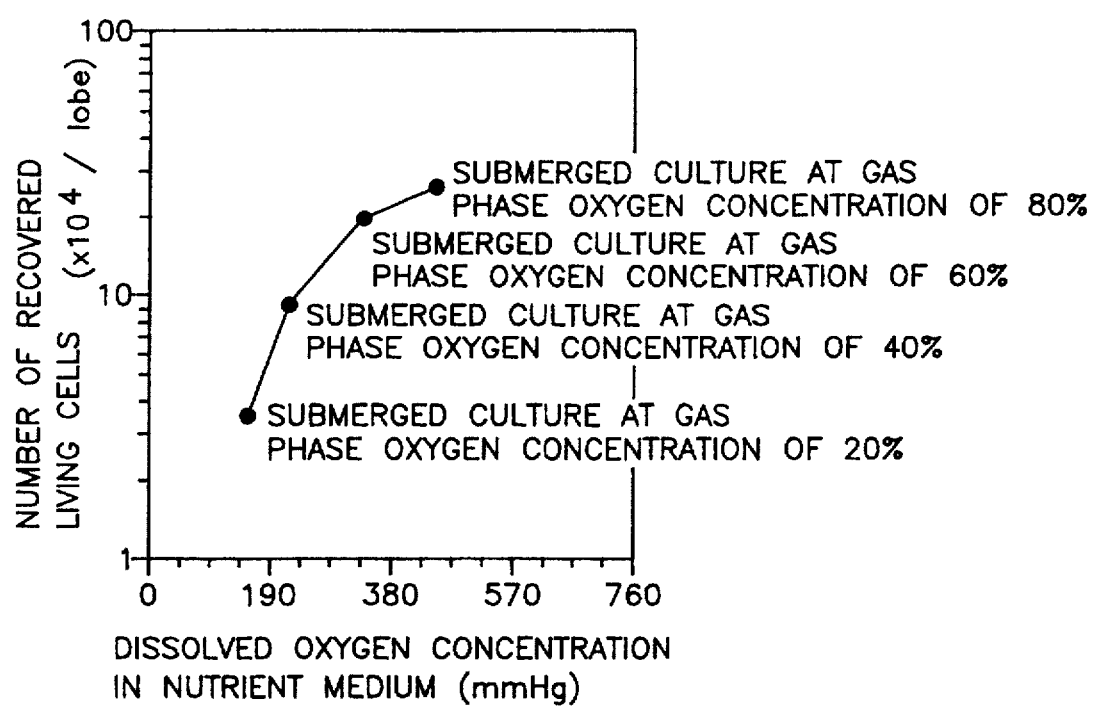
FIG. 1 is a graph showing a correlation between the number of recovered viable cells and the dissolved oxygen concentration in a nutrient medium under each culture condition. Each data point represents culture at a different gas phase oxygen concentration. From left to right: gas phase oxygen concentration of 20% (corresponds to dissolved oxygen concentration of about 143 mmHg); gas phase oxygen concentration of 40% (corresponds to dissolved oxygen concentration of about 214 mmHg); gas phase oxygen concentration of 60% (corresponds to dissolved oxygen concentration of about 333 mmHg); gas phase oxygen concentration of 40% (corresponds to dissolved oxygen concentration of about 451 mmHg).
Figure 2:
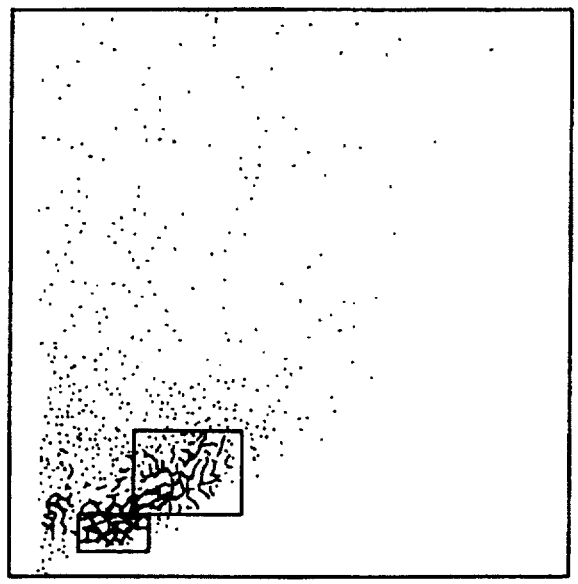
FIGS. 2 to 7 are graphs showing the distributions of the following various types of cells, which is distinguished on the basis of cell sizes determined by using a flow cytometer, wherein relative complexities of the cells based on side-light scatter are plotted along the ordinates and relative cell sizes based on forward-light scatter are plotted along the abscissas; That is.
Figure 3:
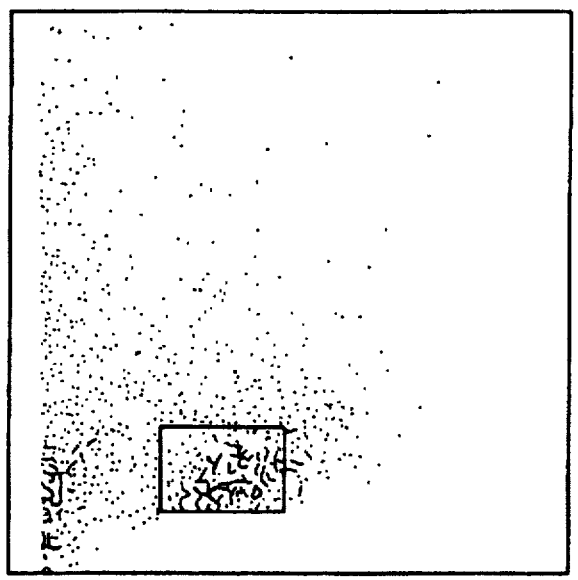
Figure 4:
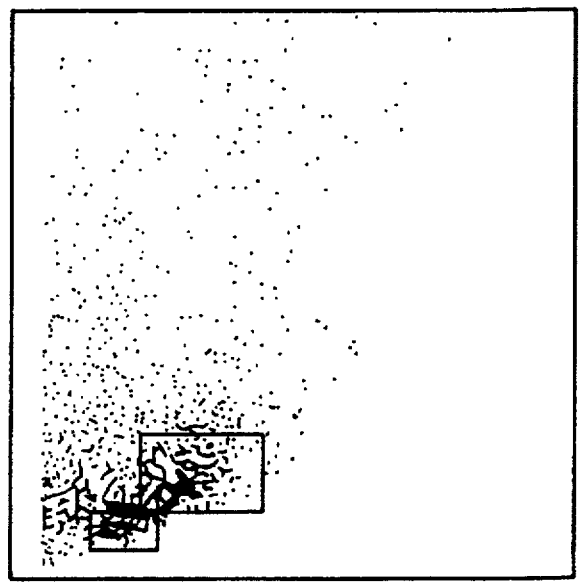
Figure 5:
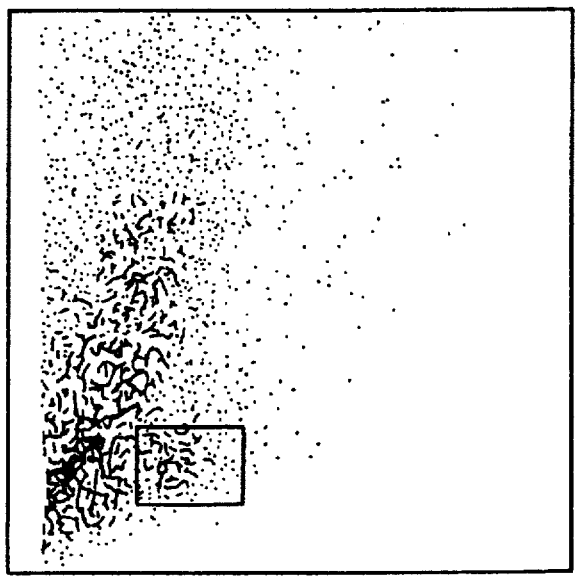
Figure 6:
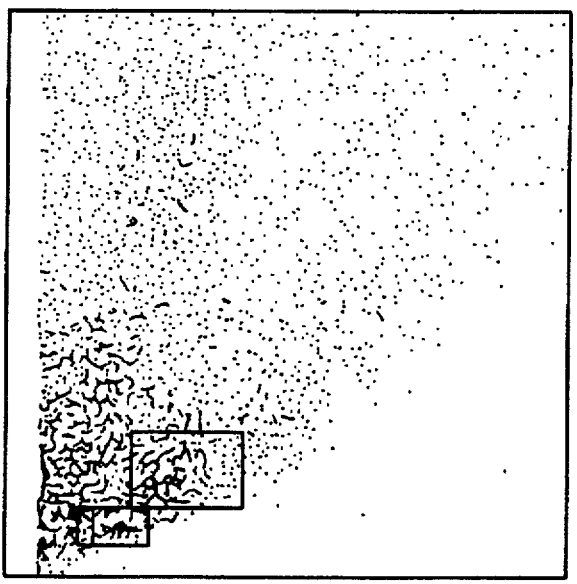
Figure 7:
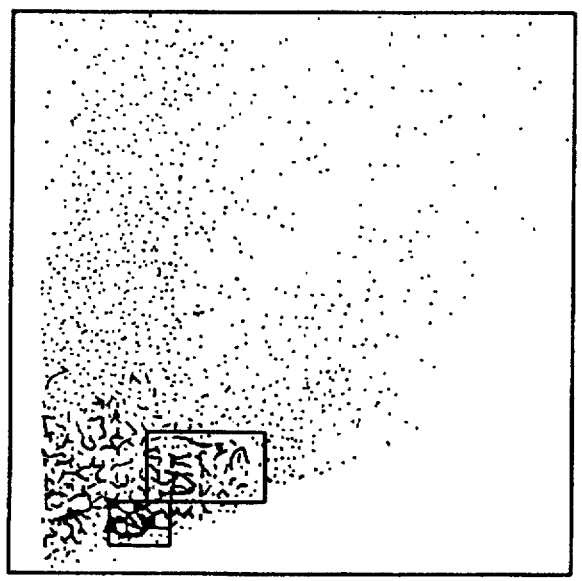
Figure 8:
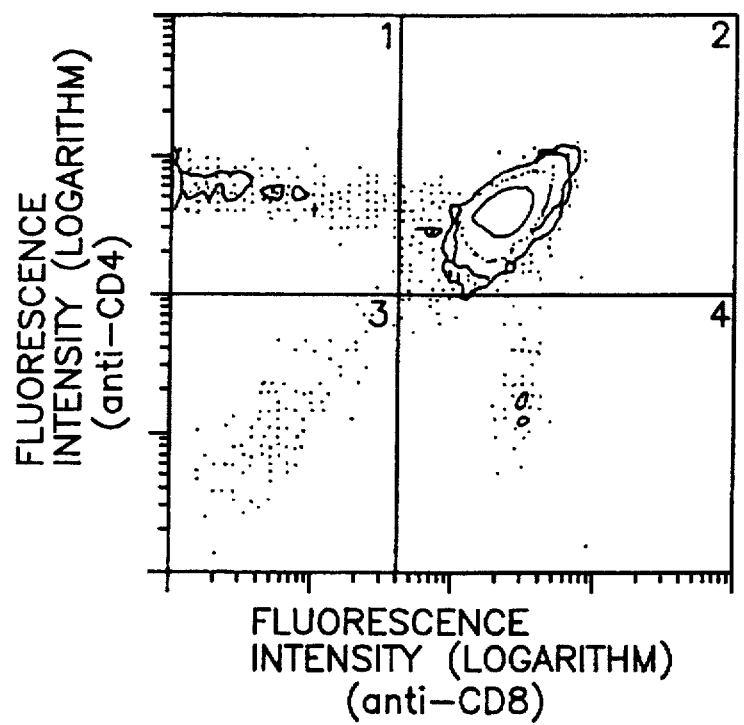
FIGS. 8 to 15 are graphs showing the cell distributions showing the expression level of CD4 and/or CD8, each of which is a differentiation antigen on mouse T cell membranes. These expression levels are distinguished by a fluorescence-linked antibody-mediated analysis using a flow cytometer, wherein the expression level of CD4 is plotted along the ordinates and the expression level of CD8 is plotted along the abscissas; that is.
Figure 9:
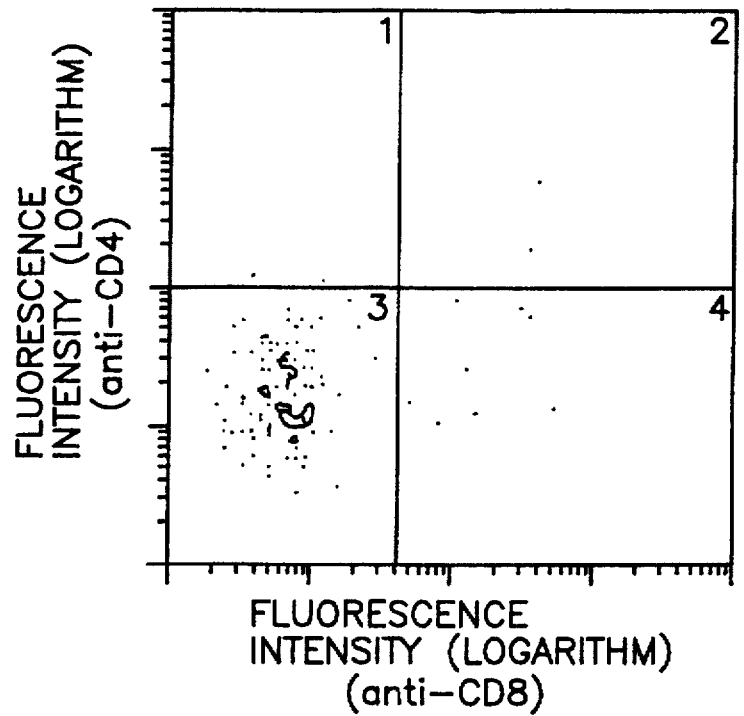
Figure 10:
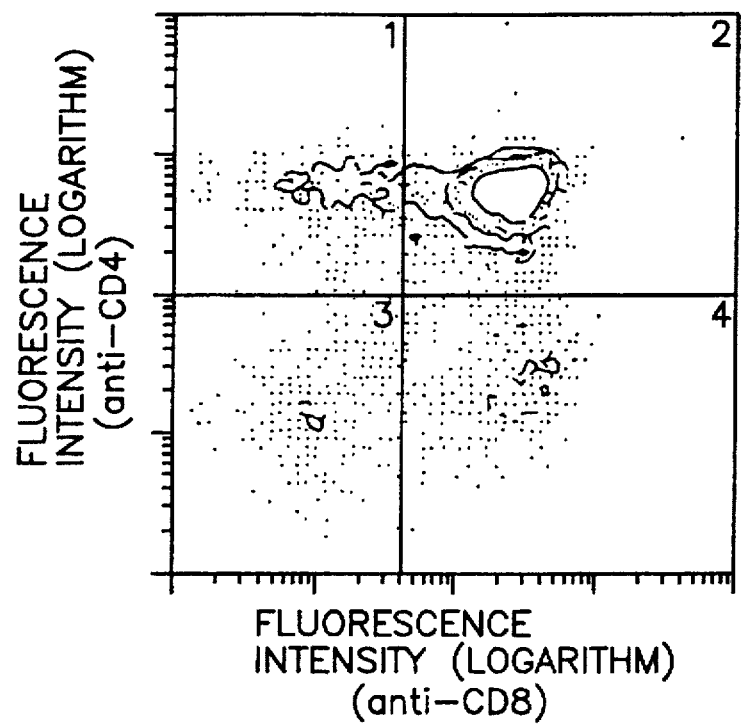
Figure 11:
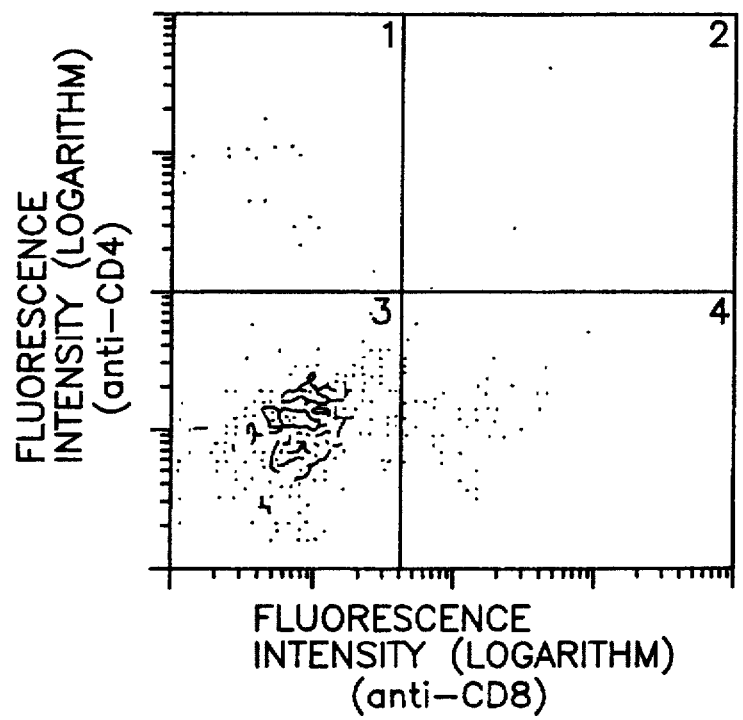
Figure 12:
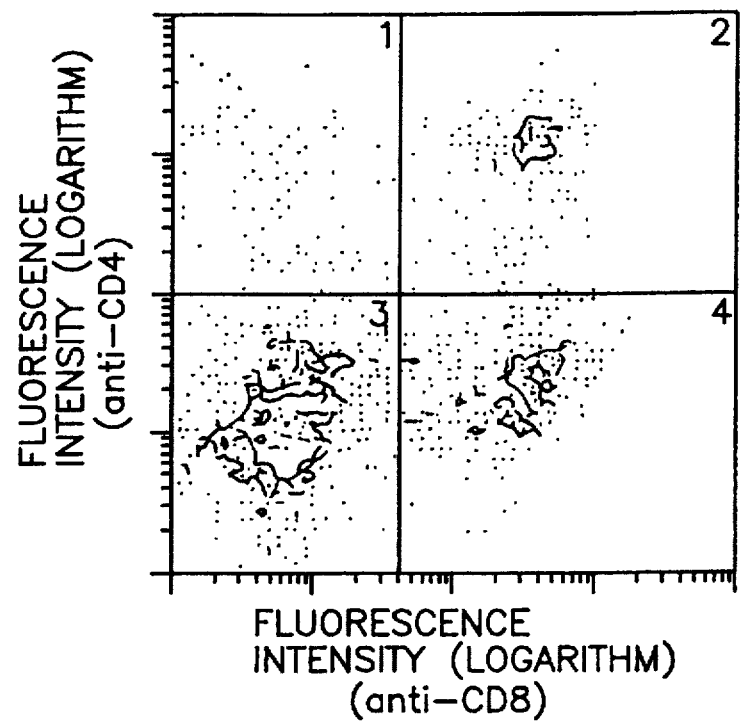
Figure 13:
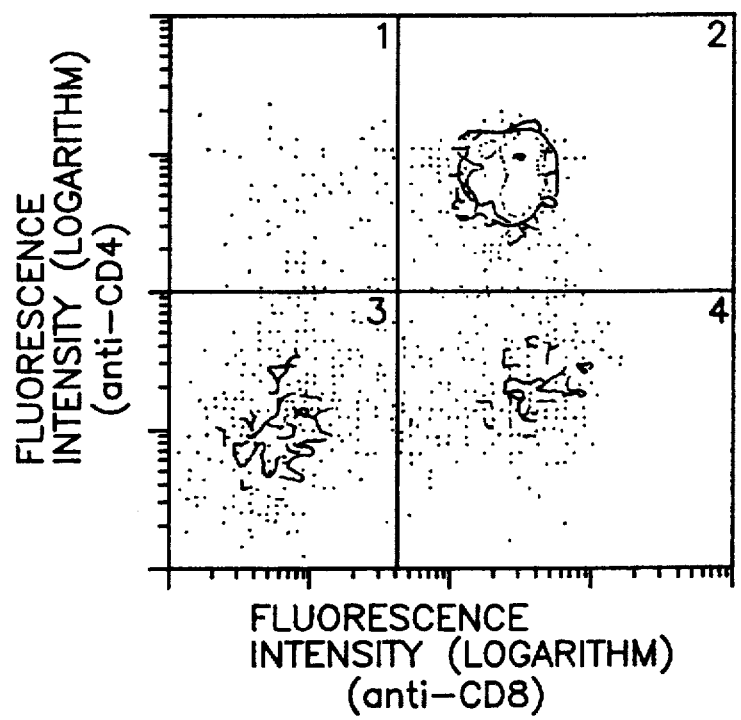
Figure 14:
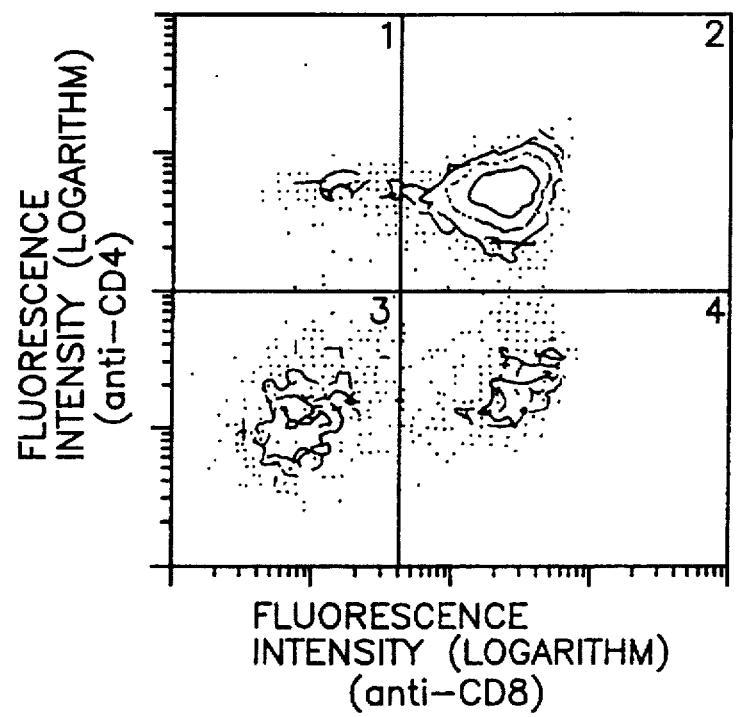
Figure 15:
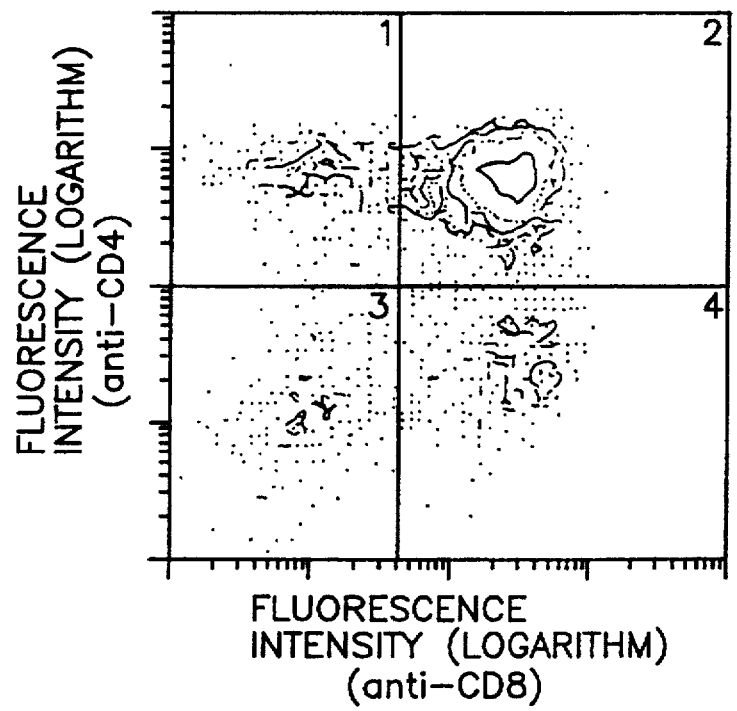

Results are summarized in Table 1. In order to examine the relationship between the numbers of recovered viable cells of each population of cells after the culture and the dissolved oxygen concentration in the nutrient medium, the dissolved oxygen concentrations in the medium after completion of the culture were measured by a blood gas analyzer (Stat Profile available from Biomedical Corp.), and results are shown in FIG. 1.

TABLE 1

| Gas Phase Concentration (vol %) | | | Number of Cells after Culture (× 10$^4$/lobe) | | | |
|---|---|---|---|---|---|---|
| O$_2$ | N$_2$ | CO$_2$ | Experiment 1 | Experiment 2 | Experiment 3 | Average Value |
| afloat culture | | | | | | |
| 20 | 75 | 5 | — | 34.4 | 32.0 | 33.2 |
| submerged culture | | | | | | |
| 5 | 90 | 5 | 2.7 | — | 2.0 | 2.4 |
| 20 | 75 | 5 | 4.7 | 3.0 | 3.5 | 3.7 |
| 30 | 65 | 5 | 7.3 | — | — | 7.3 |
| 40 | 55 | 5 | 11.7 | 6.9 | — | 9.3 |
| 60 | 35 | 5 | 17.5 | 27.6 | 25.5 | 23.5 |
| 80 | 15 | 5 | — | 28.5 | 29.0 | 28.8 |

The cells proliferated up to about 33.2×10⁴ cells/lobe on the fifth day by the conventional afloat culture, namely, 5-times cell proliferation was observed in comparison with the state prior to the culture.

On the other hand, in the submerged culture, the cell proliferation only up to about 2.4×10⁴ cells/lobe and 3.7× 10⁴ cells/lobe were observed at oxygen concentrations of 5% and 20%, respectively. In contrast, the cells significantly proliferated at an oxygen concentration of 40% or more. At oxygen concentrations of 40%, 60% and 80% respectively, proliferations up to about 9.3×10⁴ cells/lobe, 23.5×10⁴ cells/lobe, and 28.8×10⁴ cells/lobe were observed. In particular, the cells multiplied about 4 times in comparison with the state prior to the culture at the oxygen concentration of 80%. The cell proliferation at the oxygen concentration of 80% was almost equal to that of the conventional cumbersome afloat culture which was not suitable for mass production due to the complexity of the process.

EXAMPLE 2

Differentiation of T precursor cells (Expression of Differentiation Antigens)

Following the same procedures as in 1–3 above, air available in a vessel was substituted with gas mixtures (from Iwatani Sangyo Inc.) containing 5% carbon dioxide and 5% oxygen, 5% carbon dioxide and 20% oxygen, 5% carbon dioxide and 40% oxygen, 5% carbon dioxide and 60% oxygen, and 5% carbon dioxide and 80% oxygen. Then, cells were cultured in the vessel using a submerged culture and differentiation states of the grown cells were examined.

In order to compare the present invention with the prior art, cells were cultured by an afloat culture following the same procedures as in 1–3 above to examine the differentiation states.

Mouse matured T cells were used as a control.

<2-1> Distribution of Cells

The distribution of cells was measured by a flow cytometer (FACScan available from Becton Dickinson Corp.) to observe the differentiation states of the cultured T precursor cells.

Results are shown in FIGS. 2 to 7.

In these experiments, the distribution of cells roughly classified into blastic lymphoid cells, whose differentiation and maturation have not been completed, and small lymphoid cells whose differentiation and maturation have been completed and have a diameter of about 5 to 10 µm is examined. By this examination of the cell distribution, it is able to observe the state of the differentiation and maturation of the T precursor cells.

Most of the cells in the population of mouse matured T cells (FIG. 2) were observed as small lymphoid cells. Similarly, in a population of cells (FIG. 4) obtained by culturing mouse fetal thymuses by an afloat culture at an oxygen concentration of 20%, most of the cells were observed as small lymphoid cells.

On the other hand, in populations of cells (FIGS. 5 and 6) obtained by culturing mouse fetal thymuses by a submerged culture at oxygen concentrations of 5% and 20% respectively, most of the cells were observed as blastic lymphoid cells similar to the case of a population of the mouse fetal thymocytes (FIG. 3) immediately after being collected. The result showed that the differentiation and maturation were not achieved.

On the contrary to those results, in a population of cells (FIG. 7) cultured by a submerged culture at an oxygen concentration of 60%, most of cells were observed as small lymphoid cells similar to the cases of a population of mouse matured T cells (FIG. 2) and the population of cells (FIG. 4) cultured by an afloat culture at an oxygen concentration of 20%. The result showed that the differentiation and maturation of the T precursor cells were achieved.

<2-2> Expression of Differentiation Antigens

Expression level of mouse differentiation antigens CD4 and CD8 were measured by an ordinary method using a flow cytometer (FACScan available from Becton Dickinson Corp.) in accordance with a fluoresance-linked antibody-mediated analysis using monoclonal antibodies for each differentiation antigen of the mouse T cells, in order to observe the differentiation level of the T precursor cells after the culture.

The monoclonal antibodies used in this experiment were a phycoerythrin (PE)-labeled anti-mouse CD4 monoclonal antibody (rat hybridoma GK1.5 available from Becton Dickinson Corp.) and a fluorescein isothiocyanate (FITC)-labeled anti-mouse CD8 monoclonal antibody (rat hybridoma 53.6.7 available from Becton Dickinson Corp.)

Results are shown in Table 2 and FIGS. 8 to 15.

TABLE 2

| Gas Phase Oxygen Concentration (vol %) | Persentage of Cells Expressing Differentiation Antigens (CD4 and/or CD8 positive) | |
|---|---|---|
| | Persentage to whole viable cells | Percentage to blastic lymphoid cells |
| afloat culture | | |
| 20 | 97.9 | 90.5 |
| submerged culture | | |
| 5 | 16.7 | 16.7 |
| 20 | 59.3 | 34.3 |
| 40 | 84.1 | 56.2 |
| 60 | 92.6 | 69.8 |
| 80 | 96.4 | 81.1 |

Most of cells in the population of mouse matured T cells (FIG. 8) were found to be CD4⁺ and/or CD8⁺. Further, most of these cells were CD4⁺ CD8³⁰. Similarly, in a population of cells (FIG. 10) obtained by culturing mouse fetal thymocytes by an afloat culture at an oxygen concentration of 20%, 90% or more cells of total cells were found to be CD4⁺ and/or CD8⁺.

On the other hand, in populations of cells (FIGS. 11 and 12) obtained by culturing mouse fetal thymocytes by a submerged culture at oxygen concentrations of 5% and 20% respectively, most of the cells were CD4⁻ CD8⁻. The cells were, therefore, kept undifferentiated in terms of phenotypes of the differentiation antigens similar to the case of a population of mouse fetal thymocytes (FIG. 9) immediately after being collected.

In contrast to these populations of cells, in a population of cells (FIG. 13) cultured by a submerged culture at an oxygen concentration of 40%, 80% or more of the total cells were CD4⁺ and/or CD8⁺. In populations of cells (FIGS. 14 and 15) cultured by a submerged culture at oxygen concentrations of 60% and 80% respectively, 90% or more of the total cells were CD4⁺ and/or CD8⁺ similar to the cases of the populations of cells (FIG. 8) obtained by culturing the populations of mouse matured T cells (FIG. 8) and the populations of cells (FIG. 10) cultured by an afloat culture at an oxygen concentration of 20%. Moreover, most of the cells in the populations of cells in FIG. 13 were CD4⁺ CD8⁺. The results showed that the differentiation and maturation of the T precursor cells in terms of phenotypes of the differentiation antigens were achieved.

In addition, the ratio of cells expressing the differentiation antigens in the population of blastic lymphoid cells were increased as the oxygen concentration was raised in the submerged culture. In the population of blastic lymphoid cells cultured by submerged culture at oxygen concentrations of 60% and 80%, 70 to 80% of the total cells expressed the differentiation antigens.

The above results were similar to the ratio of cells expressing differentiation antigens in the population of blastic lymphoid cells obtained by performing an afloat culture at an oxygen concentration of 20%, indicating that the differentiation in terms of phenotypes of the differentiation antigens was almost perfectly achieved.

<2-3> Expression of T cell Receptor

At one stage of differentiation and maturation, the T precursor cells express an antigen receptor (T cell receptor; TcR) on the cell membrane. The TcR consists of subunits called $\alpha$-, $\beta$-, $\gamma$- and $\delta$ chains. TcR associates with CD3, which is one differentiation antigen serving as a molecule for intracellular signal transduction, thereby forming CD3-TCR. Therefore, by examining the expressions of TcR$\alpha\beta$ and TcR$\gamma\delta$ and the expression of CD3, the differentiation level and the degree of the functional maturation can be evaluated. The T cells providing a recognition mechanism for foreign antigens are mainly the cells expressing TcR$\alpha\beta$. The thymus produces a larger number of TcR$\alpha\beta$-expressing T cells than of TcR$\gamma\delta$-expressing T cells and supplies the periphery with TcR$\alpha\beta$-expressing T cells.

In this experiment, the expression levels of CD3, TcR$\alpha\beta$ and TcR$\gamma\delta$ were examined following the same procedures as in 2-2 above by using monoclonal antibodies for their differentiation antigens; CD3, TcR$\alpha\beta$ and TcR$\gamma\delta$ respectively.

The monoclonal antibodies used in this experiment were an anti-mouse CD3 monoclonal antibody (hamster hybridoma 145-2C11 available from Seikagaku Kogyo Inc.), an anti-mouse TcR$\alpha\beta$ monoclonal antibody (hamster hybridoma H57-597), and an anti-mouse TcR$\gamma\delta$ monoclonal antibody (hamster hybridoma 3A10). A fluorescein-labeled rabbit anti-hamster immunoglobulin (available from Caltag Corp.) was used as a secondary antibody.

Results are shown in Table 3.

TABLE 3

| Form of Culture | Gas Phase Oxygen Concentration (vol %) | Percentage of Cells Expressing Antigens (Number of Cells Expressing Antigens; × 10⁴) | | |
|---|---|---|---|---|
| | | CD3 | TcR$\alpha\beta$ | TcR$\gamma\delta$ |
| Before Culture | — | 2.3 (0.16) | 0.3 (0.02) | 2.1 (0.15) |
| After afloat culture | 20 | 55.7 (19.9) | 48.8 (17.4) | 4.7 (1.70) |
| After submerged culture | 5 | 45.9 (0.96) | 11.3 (0.24) | 28.5 (0.60) |
| | 20 | 49.2 (1.70) | 19.3 (0.68) | 24.3 (0.85) |
| | 60 | 63.2 (12.6) | 46.9 (9.40) | 14.4 (2.90) |

As for the expression of CD3, ratio of CD3-positive cells was 63.2% in a population of cells cultured by a submerged culture at an oxygen concentration of 60%. This expression ratio was equal to or higher than the expression ratio of 55.7% in the population of cells cultured by an afloat culture at an oxygen concentration of 20%, thus indicating that the differentiation of the T precursor cells was achieved.

The expressions of TcR$\alpha\beta$ and TcR$\gamma$6 occurred as follows. The TcR$\alpha\beta$-expressing cells and TcR$\gamma\delta$-expressing cells were respectively 48.8% and 4.7% in the population of cells cultured by an afloat culture at an oxygen concentration of 20%. That is, the differentiation of the TcR$\alpha\beta$-expressing T cells occurred selectively.

On the other hand, the TcR$\alpha\beta$-expressing cells were respectively 11.3% and 19.3% in the population of cells cultured by a submerged culture at oxygen concentrations of 5% and 20%, while the TcR$\gamma\delta$-expressing cells were 28.5% and 24.3% in these populations of cells. The differentiation to TcR$\gamma\delta$-expressing T cells mainly occurred, and the differentiation to the TcR$\alpha\beta$-expressing T cells was insufficient.

In contrast to these results, the TcR$\alpha\beta$-expressing cells and TcR$\gamma\delta$-expressing cells were respectively 46.9% and 14.4% in a population of cells cultured by a submerged culture at an oxygen concentration of 60%. The differentiation to the TcR$\alpha\beta$-expressing T cells selectively occurred equally to that of the population of cells cultured by the afloat culture at the oxygen concentration of 20%, and indicating that normal differentiation of the T precursor cells was achieved.

In addition, the numbers of the recovered cells expressing CD3, TcR$\alpha\beta$ and TcR$\gamma\delta$ respectively, which were generated by the culture under the respective culture conditions were counted. CD3-, TcR$\alpha\beta$-, and TcR$\gamma\delta$-expressing cells were not sufficiently observed in populations of cells cultured by a submerged culture at oxygen concentrations of 5% and 20% respectively. However, CD3-positive and TcR$\alpha\beta$-positive cells were generated by 7 to 13 times and by 14 to 39 times, respectively, in a population of cells cultured by a submerged culture at an oxygen concentration of 60%. This result is almost equal to the result in the case of the population of cells cultured by the afloat culture at the oxygen concentration of 20%.

EXAMPLE 3

Generation of Functional T cells

<3-1> Proliferation Activity of Functional T cells Induced with Mitogen

Substances which activate lymphocytes and induce DNA synthesis and cell proliferation are generically called mitogens (division accelerating factor). Concanavalin-A (ConA), one of the mitogens, acts through a CD3-TcR (shown in 2-3) complex which participates in antigen recognition on the T cells, thereby inducing the proliferation of T cells. The proliferation of the T cells induced by ConA is maintained by cytokines such as Interleukin-2 (IL-2) which is secreted into the culture supernatant from the T cells upon ConA stimulus.

In this experiment, following the same procedures as in 2-3 described above, thymuses were cultured for 5 days at various oxygen concentrations, using a 24-well microtiter plate. Thus obtained T cells were cultured in an RPMI-1640 complete medium containing a 10% FCS in the presence of ConA (15 mg/ml available from Vector Corp.) and IL-2 (50 units; available from Genzyme Corp.) using a 96-well microtiter plate, and then, derivation and generation of functionally matured T cells having ConA reactivity were examined.

The ConA reactivity of the T cells was determined as follows. The cultures were performed for 3 days, then, 1.0 μCi of tritium-labeled thymidine ($^3$H-TdR) was added to each medium at 6 hours before from the end of the culture, and cells were harvested onto glass filters. Then, a scintillator (Clear-SolI available from Nakarai Techs Inc.) was added to each sample, and intracellular incorporation of the $^3$H-TdR was measured using a liquid scintillation counter.

Figure 16:
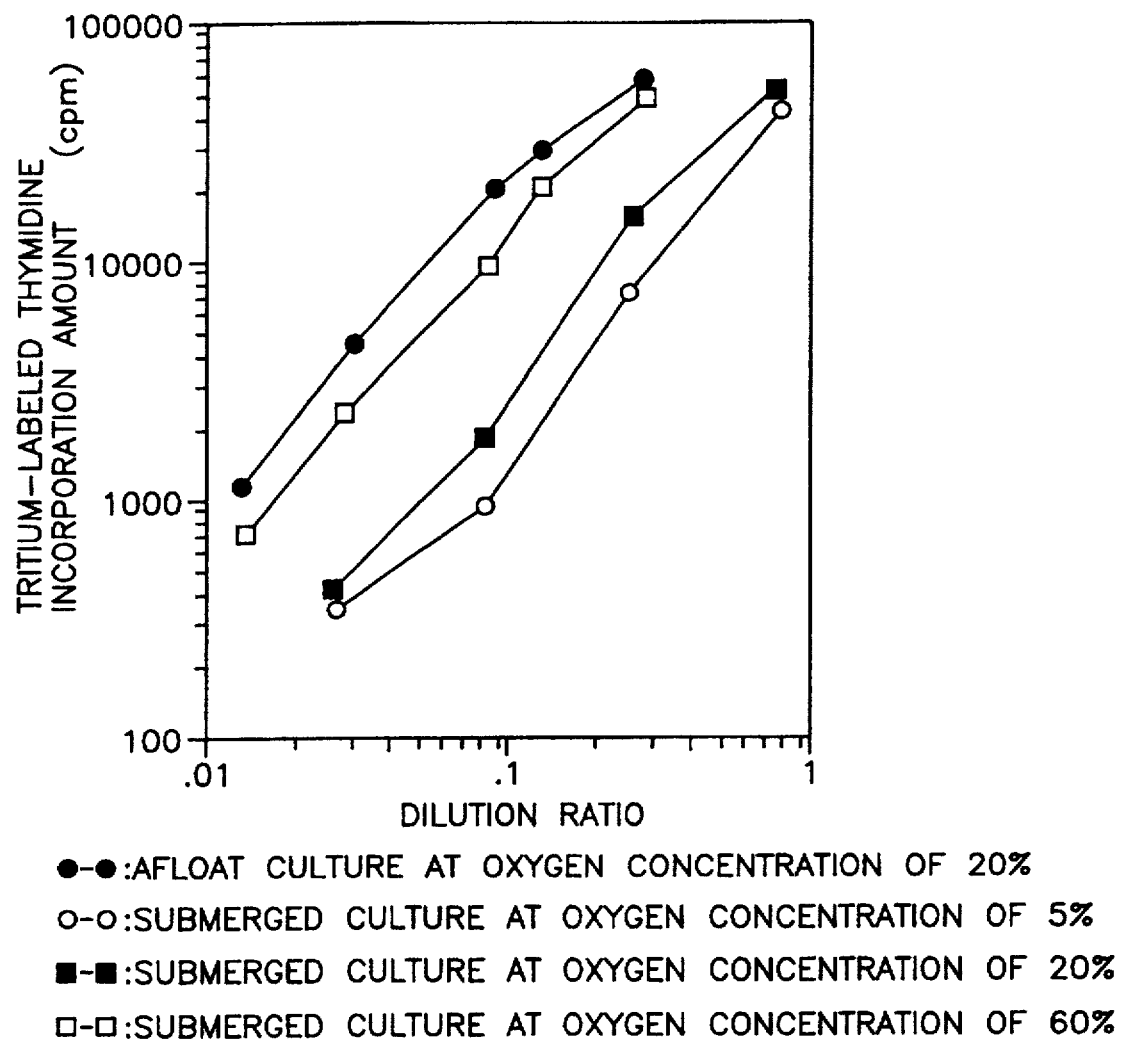
FIG. 16 is a graph showing the proliferation degree of ConA-reactive, functional T cells measured by using a tritium-labeled thymidine ($^3$H-TdR) incorporation test, wherein the cellular incorporation amounts (cpm) of $^3$H-TdR as an index of DNA synthesis accompanying in T cell proliferation are plotted along the ordinate, and the dilution rates of the number of cells per a cell population of thymus after the culture are plotted along the abscissa. ●-●: afloat culture at oxygen concentration of 20%, ○-○: submerged culture at oxygen concentration of 5%, ■-■: submerged culture at oxygen concentration of 20%, □-□: submerged culture at oxygen concentration of 60%.

Results are shown in FIG. 16.

The proliferation of populations of cells cultured by a submerged culture at oxygen concentrations 5% and 20% were ¼ to ⅓ respectively in comparison with that of a population of cells cultured by an afloat culture at an oxygen concentration of 20%. On the contary, the proliferation of a population of cells cultured by a submerged culture at an oxygen concentration of 60% was almost equal to that in the case of a population of cells cultured by an afloat culture at an oxygen concentration of 20%, showing that the functionally matured T cells having the ConA reactivity were derived and generated at the same degree with the differentiation in the thymuses of young mice and the differentiation in the fetal thymuses by the afloat culture.

<3-2> Reactivity of Functional T cells against Allo (BALB/C Mouse) Spleen Cells

T cells are educated in the thymus and acquire reactivity against allo mouse cells which are non-self, thereby causing graft rejection, for example. Similarly to the action of ConA described in 3-1 above, this reaction is also caused via a TcR-CD3 complex on the T cells which have matured in the thymus.

In this experiment, thymuses were cultured for 6 days at various oxygen concentrations, using 24-well microtiter plates as in the method in 2-3 above. T cells thus obtained were cultured in a 96-well microtiter plate ($5\times10^5$ cells/well), to which were added cell suspensions which were obtained by pretreating spleen cells collected from 6-week old BALB/C mice with mitomycin C (25 µg/ml, 37° C., 30 minutes), subsequently washing the treated cells with an RPMI-1640 medium three times. Then, generation of the T cells having reactivity against the allo cells was examined.

The allo reactivity of the T cells was determined as follows. The cultures were performed for 5 days, then, 1.0 µCi of tritium-labeled thymidine ($^3$H-TdR) was added to each medium at 6 hours before the end of the culture, and cells were harvested onto glass filters. A scintillator (Clear-SolI available from Nakarai Techs Inc.) was added to each sample, and intracellular incorporation of the $^3$H-TdR was measured using a liquid scintillation counter.

Figure 17:
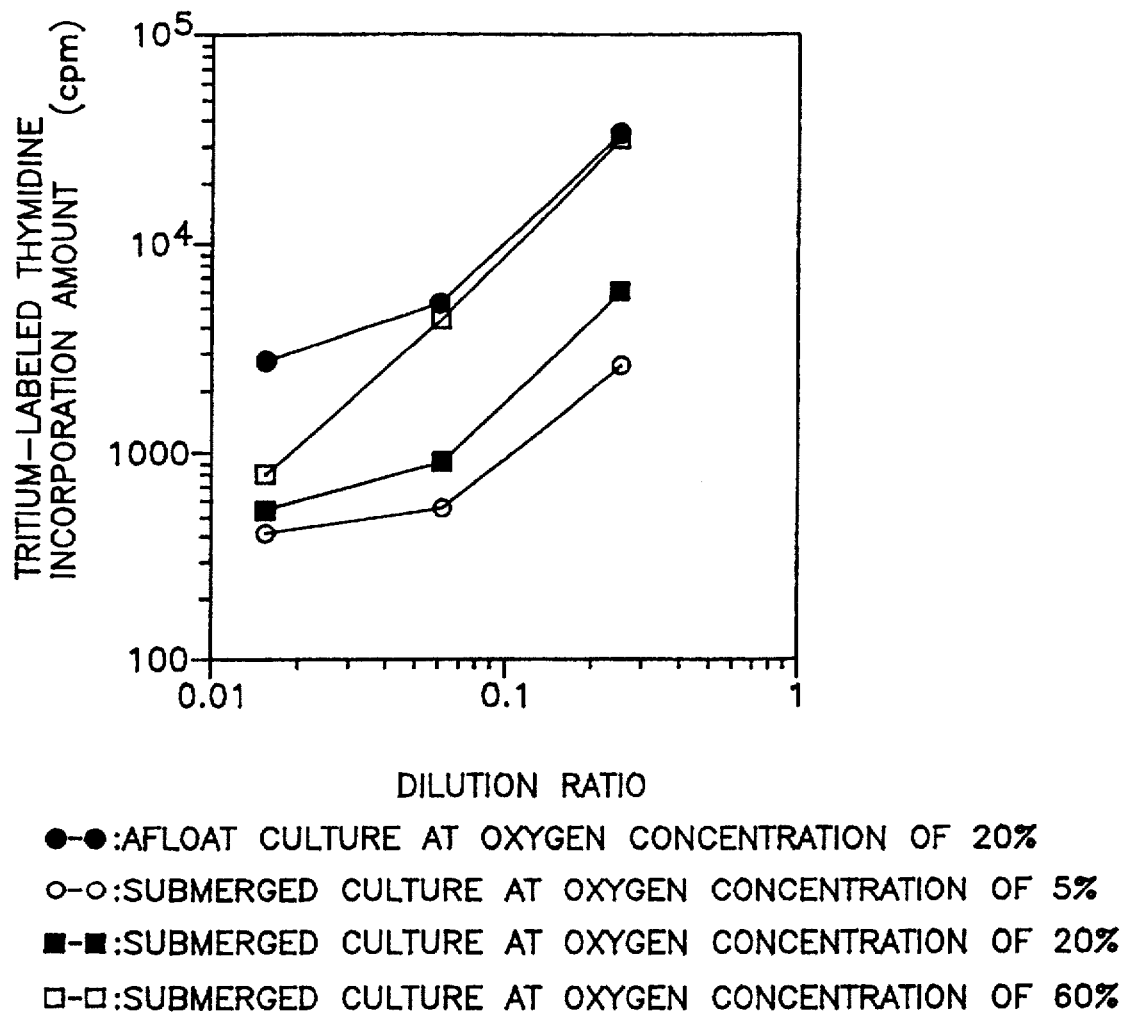
FIG. 17 is a graph showing the proliferatrion degree of allo-reactive, functional T cells measured by using a tritium-labeled thymidine ($^3$H-TdR) incorporation test, wherein the cellular incorporation amounts (cpm) of $^3$H-TdR as an index of DNA synthesis accompanying in T cell proliferation are plotted along the ordinate, and the dilution rates of the number of cells per a cell population of thymus after the culture are plotted along the abscissa. ●-●: afloat culture at oxygen concentration of 20%, ○-○: submerged culture at oxygen concentration of 5%, ■-■: submerged culture at oxygen concentration of 20%, □-□: submerged culture at oxygen concentration of 60%.

Results are shown in FIG. 17.

The proliferation of populations of cells cultured by a submerged culture at oxygen concentrations 5% and 20% were 1/10 to 1/5 compared with that of a population of cells cultured by an afloat culture at an oxygen concentration of 20%. In contrast to the results, the proliferation of a population of cells cultured by a submerged culture at an oxygen concentration of 60% was almost equal to that of a population of cells cultured by an afloat culture at an oxygen concentration of 20%, which indicated that the functionally matured T cells having the allo reactivity were derived and generated at the same degree with the differentiation in the thymuses of young mice and the differentiation in the fetal thymuses by the afloat culture.

EXAMPLE 4

Differentiation and Maturation of T precursor cells by Combination of T precursor cells and Interstitial Cells of Lymphoid Tissues Normal differentiation and maturation of T precursor cells using mouse fetal thymuses by applying the technique of the present invention have been described in Examples 1 to 3. According to the present invention, furthermore, normal differentiation and maturation of T precursor cells can be also achieved by using a combination of T precursor cells and interstitial cells of lymphoid tissues (e.g., thymic epithelial cells, fibroblasts, other interstitial cells of lymphoid tissues, and/or intercellular substances) surrounding the T precursor cells which are respectively collected from the same or different individuals of the same or different species. An example is described below.

Thymuses obtained from 15-day fetuses of B6 mice (available from Nippon SLC Corp.) were cultured by an afloat culture in RPMI-1640 complete medium containing 1.35 mM 2'-deoxyguanosine (dGuO) and 10% fetal calf serum (FCS) for 6 days, followed by further afloat culture for 12 hours in the complete medium without dGuO, thereby obtaining thymic interstitial cells free from blood cells.

The thymic interstitial cells thus obtained were seeded in a 96-well round bottom plate, and RPMI-1640 complete medium was added to the plate (200 µl/well). Then, T precursor cells (mouse fetal thymocytes) obtained b the same procedures as in Example 1-2 were added at 30 cells/well or 300 cells/well. The plate was sealed in a plastic vessel (Gaspack available from BBL Corp.), and air in the vessel was substituted with gas mixture (available from Iwatani Sangyo Inc.) containing 5% of carbon dioxide, 60% of oxygen, and 35% of nitrogen. Thereafter, the samples were cultured by a submerged culture for 7 days.

After the culture, the recovered cells and the thymic tissues were gently minced with a stainless steel mesh to obtain T cells. In order to observe the differentiation and maturation degree of T precursor cells after the culture, the expression level of CD4 and CD8, which are differentiation antigens of the mouse T cells, was measured following the same procedures as in Example 2-2.

A culture obtained by culturing only thymic interstitial cells without adding the T precursor cells (mouse fetal thymocytes) by a submerged culture at an oxygen concentration of 60% was used as a control, and mouse matured T cells were used for comparison.

Figure 18:
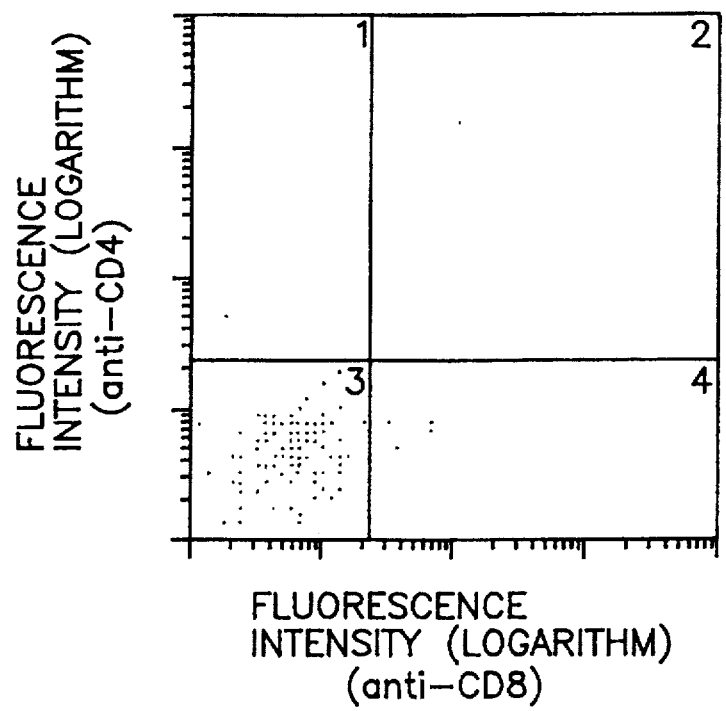
FIG. 18 is a graph showing the cell distribution which represents the expression level of CD4 and/or CD8 after mouse thymic interstitial cells not containing mouse fetal thymocytes is cultured by a submerged culture at a 60% oxygen concentration.
Figure 19:
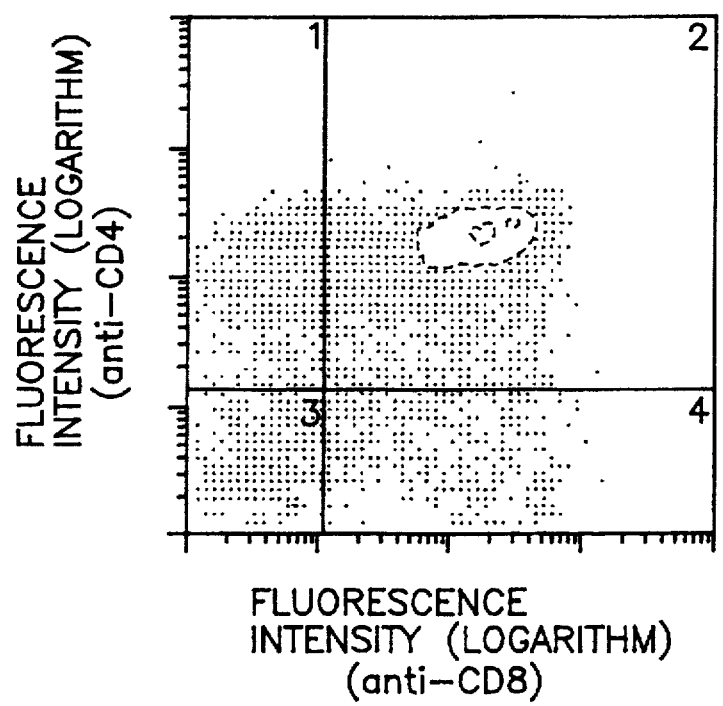
FIG. 19 is a graph showing the cell distribution which represents the expression level of CD4 and/or CD8 after individually collected mouse thymic interstitial cells and 300 mouse fetal thymocytes are cultured by a submerged culture at a 60% oxygen concentration.
Figure 20:
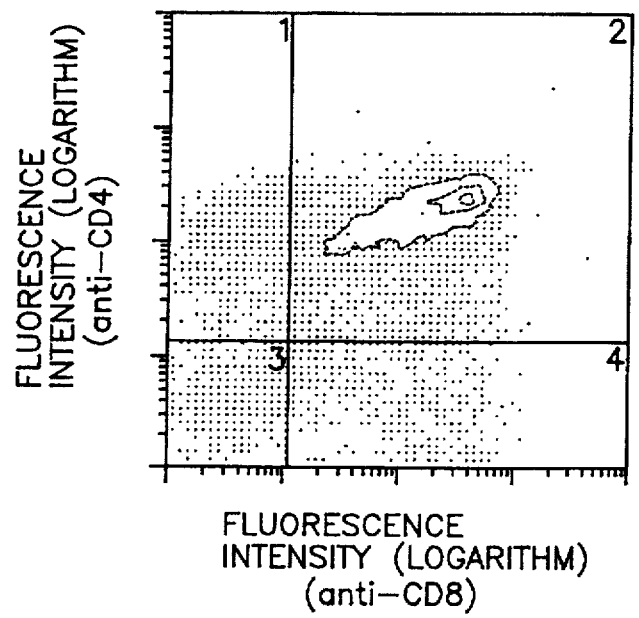
FIG. 20 is a graph showing the cell distribution which represents the expression level of CD4 and/or CD8 of mouse matured T cells.

Results are shown in FIGS. 18 to 20.

Most of the cells in the population of mouse matured T cells group (FIG. 20) were $CD4^+$ and/or $CD8^+$. Further, most of these cells were $CD4^+$ $CD8^+$.

In the population of cells (FIG. 18) cultured by a submerged culture at an oxygen concentration of 60% without adding the T precursor cells (mouse fetal thymocytes), very few cells (including thymic epithelial cells, fibroblasts, and so on) were recovered, very few cells exhibited $CD4^+$ and/or $CD8^+$.

On the other hand, in the populations of cells obtained from the culture by a combination of mouse thymic interstitial cells and T precursor cells (mouse fetal thymocytes) (30 or 300 cells each), which were individually collected, by a submerged culture at an oxygen concentration of 60%, a large number of cells were found to be $CD4^+$ and/or $CD8^+$. When 30 cells/well mouse fetal thymocytes were used, 30 to 40% cells exhibited $CD4^+$ and/or $CD8^+$. When 300 cells/well of mouse fetal thymocytes were used (FIG. 19), 90% or more of the cells exhibited $CD4^+$ $CD8^+$.

The result in the culture by combination is equivalent to that in the case of the population of mouse matured T cells, showing that the differentiation and maturation of the T precursor cells in terms of their phenotypes of the differentiation antigens were achieved even by a culture with a combination of the mouse fetal thymocytes and the mouse thymic interstitial cells which were individually collected.

EXAMPLE 5

Culture of Allogenic T precursor cells in Matured T cells Deficient Animal Model When the thymus functions for proliferating, differentiating, and maturing B precursor cells and/or T precursor cells are deficient or the matured B cells and/or the matured T cells are congenitally deficient, various diseases owing to a deficient immune system are induced. Even if the matured B cells or matured T cells were administered in an adoptive immunotherapy, matured B cells or matured T cells having an appropriate antigen specificity cannot be induced due to the deficiency of lymphoid precursor cells (e.g., B precursor cells and T precursor) or the abnormality of the proliferation, differentiation, and maturation process in the thymus. Therefore, there is little significance of therapy. In order to examine the therapeutic significance value of the present invention in such a model, the following experiment was performed.

Thymuses were aseptically collected from 6-week old SCID mice (severe combined immunodeficient mouse; available from Fox Chase Corp.) which are the model of mice having defects in abilities of differentiation and maturation of B precursor cells and T precursor cells, following the same procedures as in Example 1-1. The obtained each thymus was divided into four pieces. Each piece was added to an RPMI-1640 complete medium using a 96-well microtiter plate.

Fetal thymocytes as T precursor cells were obtained from 14-day fetuses of C57BL/6 mice (available from Nippon SLC Inc.) following the same procedures as in Examples 1-1 and 1-2 and they were added by the number of $5 \times 10^4$ cells/well into the RPMI-1640 complete medium containing the thymus pieces of the SCID mouse.

The cells in the culture plate were subjected to a submerged culture at 37° C. for 7 days, in an atmosphere having a carbon dioxide concentration of 5% and an oxygen concentration of 20% (normal atmospheric condition) and in an atmosphere having a carbon dioxide concentration of 5% an oxygen concentration of 80%.

In order to improve efficiency of the differentiation and maturation of the T precursor cells, a culture was performed under the same conditions using the SCID mouse thymuses which T precursor cells having no differentiation or maturation abilities were removed by radiation (2.5 Gr).

The number of cells after culture was counted by the trypan blue dye exclusion test.

The results are shown in Table 4. Each described value is an average of experimental values obtained using four-split thymus pieces.

TABLE 4

| Gas Phase concentration (Vol %) | | | Number of cells after culture (cells/lobe) | |
|---|---|---|---|---|
| $O_2$ | $N_2$ | $CO_2$ | Radiation-Treated | Radiation-Non-Treated |
| 20 | 75 | 5 | — | $1.3 \times 10^4$ |
| 80 | 15 | 5 | — | $2.8 \times 10^4$ |
| 20 | 75 | 5 | $1.6 \times 10^4$ | — |
| 80 | 15 | 5 | $3.8 \times 10^4$ | — |

In experiments using both radiation-treated thymuses and nontreated thymuses, populations of cells cultured at an oxygen concentration of 80% exhibited twice or more of a survival rate of T precursor cells compared with that of populations of cells cultured at an oxygen concentration of 20% (normal atmospheric condition).

In comparison between the populations of cells cultured at an oxygen concentration of 80% using radiation-treated or nontreated thymuses, the population of cells using the radiation-treated thymuses exhibited a more significant survival rate of T precursor cells than the population of cells using the nontreated thymuses. Differentiated and matured T cells were observed in the viable cells.

EXAMPLE 6

Culture of Human T Precursor Cells at High Oxygen Concentration

A part of the thymus close to the heart of a 2-year old patient suffering from a heart disease was removed in a surgical operation. The obtained human thymus was divided into pieces each having a same weight (about 10 mg). The prepared thymus pieces ($5 \times 10^5$ cells/thymus piece) were treated according to the same procedures as in Example 1, followed by a submerged culture at 37° C. for 14 days in an atmosphere having a carbon dioxide concentration of 5% and an oxygen concentration of 20%, as well as in an atmosphere having a carbon dioxide concentration of 5% and an oxygen concentration of 70%.

The numbers of cells after the culture were counted by the trypan blue dye exclusion method.

Results are summarized in Table 5.

TABLE 5

| Gas Phase concentration (Vol %) | | | Number of Cells after |
|---|---|---|---|
| $O_2$ | $N_2$ | $CO_2$ | Culture (cells/lobe) |
| 20 | 75 | 5 | $0.64 \times 10^5$ |
| 70 | 15 | 5 | $1.50 \times 10^5$ |

Similar to the results of Example 1 using the mouse thymocytes, in this experiment using the human thymocytes, the survival rate of cells in the culture at the oxygen concentration of 70% (high oxygen concentration) was found to be significantly twice or more than with that found at the oxygen concentration of 20% (normal atmospheric condition).

Judging from the results obtained in Examples 5 and 6, the present invention enabled derivation of normally matured T cells from the different strain or same strain T precursor cells even in tissues such as human thymuses and matured T cell-deficient animal model such as SCID mice. Therefore, it can be given as a conclusion that the present invention is highly applicable to research and development of cell vaccines and therapeutic agents for various autoimmune diseases or immune diseases due to virus infections, such as AIDS (acquired immuno-deficiency syndrome).

EXAMPLE 7

Correlation between Gas Phase Oxygen Concentration and Liquid-Phase Dissobed Oxygen Concentration The following experiment was conducted to examine the correlation between the oxygen concentration in the gas phase contacting a nutrient medium and the dissolved oxygen concentration in the nutrient medium.

A 96-well microtiter plate containing an RPMI-1640 complete medium containing or not containing mouse fetal thymuses ($7 \times 10^4$ cells/lobe) obtained in Example 1 was sealed in a plastic vessel (Gaspack available from BBL Corp. or Tedler bag available from Seikagaku Kogyo Inc.).

Figure 21:
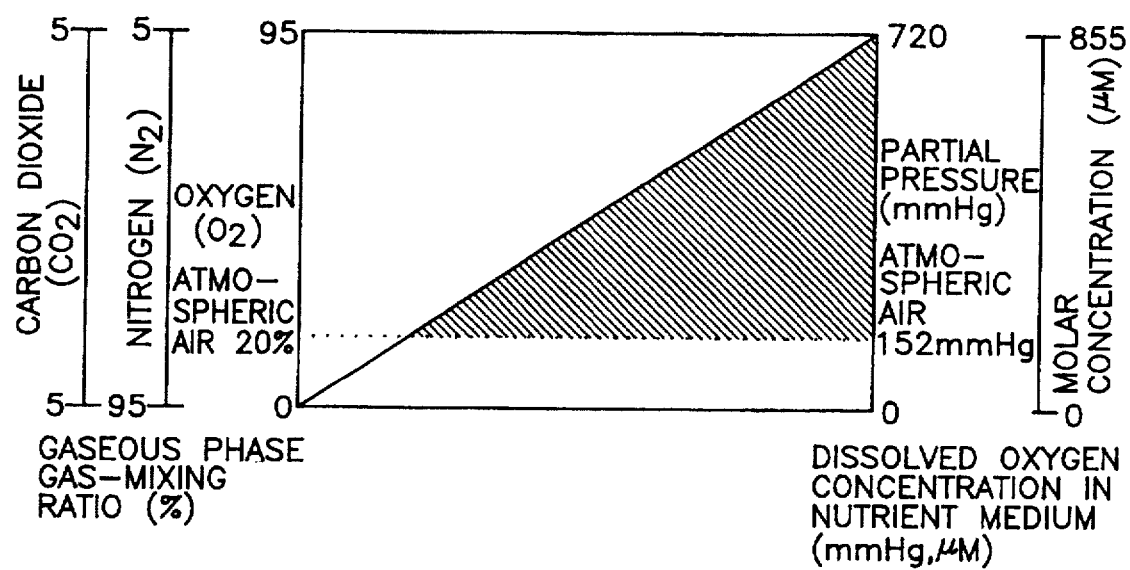
FIG. 21 is a graph showing a correlation between the oxygen concentration in the gas phase contacting with the nutrient medium and the dissolved oxygen concentration in the nutrient medium. Carbon dioxide was present in each gas mixture at a constant ratio of 5%. Oxygen in the gas phase varied from 0 to 95%, with the balance of the gas composition being nitrogen. Note that 20% oxygen is the ratio of oxygen in normal atmospheric air.

As shown in FIG. 21, the carbon dioxide concentration was maintained constant (5%), and gas mixture (available from Iwatani Sangyo Inc.) having a predetermined constant mixing ratio of the oxygen concentration (%) to the nitrogen concentration (%) was blown from a vent of the vessel to sufficiently substitute the air in the vessel with the gas mixture. Thereafter, the microtiter plate was stood in the vessel at 37° C. for 1 to 5 days.

After the concentrations of carbon dioxide, oxygen, and nitrogen were in equilibrium between the gas phase and the liquid phase, the dissolved oxygen concentration (mmHg, µM) in the nutrient medium (liquid phase) was measured using an automatic gas analyzer (available from Nova Corp.).

Results are shown in FIG. 21.

When the volume of the gas mixture (gas phase) contacting with the nutrient medium was relatively larger enough than the volume of the nutrient medium (liquid phase), a proportional relationship was obtained between the gas phase oxygen concentration and the liquid phase dissolved oxygen concentration. In addition, when the volume of the gas phase was not relatively large, it was found that a correlation falling within the region (a hatched portion in FIG. 21) below the proportional line can be established.

As has been in detail described above, according to the present invention, T lineage precursor cells are cultured in a nutrient medium under the condition that a dissolved oxygen concentration in the nutrient medium is higher than that in the nutrient medium under the normal atmospheric air, i.e., under the condition that the dissolved oxygen concentration is raised by means of raising the oxygen concentration in the gas phase contacting the nutrient medium to 40 vol% through 95 vol %. By applying the method of the invention, not only can T lineage cells be cultured in a large scale in vitro by a submerged (suspension) culture as a general method of culturing cells or tissues without using special tools, but also it is possible to realize in vitro the proliferation process of the T precursor cells and normal differentiation and maturation processes of T precursor cells in terms of the phenotypes of the differentiation antigens and their functions. It is also possible, by a submerged (suspension) culture without using special tools, to derive and generate T cells matured in terms of their phenotypes of differentiation antigens and their functions, which have appropriate antigen recognition ability tools. Therefore, the present invention can contribute to investigate details of differentiation and maturation mechanism of the T lineage cells.

Furthermore, by using the method of the present invention, T lineage precursor cells are cultured in a nutrient medium containing an antigen which induces infectious diseases such as a hepatitis virus or HIV (human immunodeficiency virus), allergic diseases, or autoimmune diseases, thereby deriving T cells which recognize the antigen. Therefore, appropriate T-cell vaccines capable of suppressing or treating the diseases such as infectious diseases, allergic diseases, and autoimmune diseases induced by the antigen can be prepared.

I claim:

1. A method to produce matured mammalian T cells specific for an antigen which induces infectious diseases, allergic diseases or autoimmune diseases, comprising a step of culturing mammalian T precursor cells or mammalian tissue containing mammalian T precursor cells together with mammalian interstitial cells of a thymus in a nutrient medium containing said antigen, said nutrient medium having a dissolved oxygen concentration ranging from 360 µM to 855 µM or contacting a gas phase having an oxygen content ranging from 40% to 95%, to obtain said matured T cells having a specificity for said antigen.

2. The method of claim 1, wherein said nutrient medium has a dissolved oxygen concentration ranging from 540 µM to 855 µM.

3. The method of claim 1, wherein said nutrient medium contacts a gas phase having an oxygen content ranging from 60% to 95%.

4. The method of claim 1, wherein said mammalian T precursor cells are obtained from a tissue of an organ selected from the group consisting of thymus, bone marrow and liver.

5. The method of claim 1, wherein said mammalian tissue containing mammalian T precursor cells is obtained from an organ selected from the group consisting of thymus, bone marrow and liver.

6. The method of claim 1, wherein said mammalian interstitial cells of a thymus and said mammalian T precursor cells or mammalian tissue containing mammalian T precursor cells are respectively obtained from a single individual.

7. The method of claim 1, wherein said mammalian interstitial cells of a thymus and said mammalian T precursor cells or said mammalian tissue containing mammalian T precursor cells are respectively obtained from different individuals of the same species.

8. The method of claim 1, wherein said mammalian interstitial cells of a thymus and said mammalian T precursor cells or said mammalian tissue containing mammalian T precursor cells are respectively obtained from individuals of different species.

9. The method of claim 1, which further comprises collecting the matured T cells so obtained.

* * * * *